United States Patent [19]

Ueda

[11] Patent Number: 4,805,598
[45] Date of Patent: Feb. 21, 1989

[54] ENDOSCOPE HAVING OPTICAL ELEMENTS THAT ARE RESISTANT TO CONDENSATION

[75] Inventor: Yasuhiro Ueda, Tokyo, Japan

[73] Assignee: Olympus Optical Co., Ltd., Tokyo, Japan

[21] Appl. No.: 99,490

[22] Filed: Sep. 22, 1987

[30] Foreign Application Priority Data

Sep. 26, 1986 [JP] Japan .................. 61-146513[U]

[51] Int. Cl.⁴ .................................................. A61B 1/06
[52] U.S. Cl. .......................................... 128/6; 350/418
[58] Field of Search ............... 128/4, 6; 350/418, 582, 350/586, 587, 589

[56] References Cited

U.S. PATENT DOCUMENTS

| 695,606 | 3/1902 | Grun | 350/418 |
|---|---|---|---|
| 3,740,113 | 6/1973 | Cass | 350/418 X |
| 4,146,019 | 3/1979 | Bass et al. | 128/6 |
| 4,286,839 | 9/1981 | Ilzig et al. | 350/418 X |
| 4,289,119 | 9/1981 | Meyer, Sr. | 350/418 X |
| 4,370,023 | 1/1983 | Lange . | |
| 4,615,333 | 10/1986 | Taguchi | 128/6 |
| 4,619,247 | 10/1986 | Inoue et al. | 128/6 |

FOREIGN PATENT DOCUMENTS

6296616  6/1987  Japan .

Primary Examiner—William H. Grieb
Attorney, Agent, or Firm—Ladas & Parry

[57] ABSTRACT

An endoscope includes an insertion section, which is inserted into a body cavity of a human subject, and image transmitting means, which is located within the insertion section and is composed a plurality of lenses. A highly-viscous gel-like substance free from any water moisture is used to fill the space between adjacent associated lenses, or else is employed as a light transmitting means for conducting light, supplied from a light source, from that distal end portion onto a body cavity of the human subject.

4 Claims, 7 Drawing Sheets

ENDOSCOPE HAVING OPTICAL ELEMENTS THAT ARE RESISTANT TO CONDENSATION

BACKGROUND OF THE INVENTION

This invention relates to an endoscope having an insertion section adapted to be inserted into a body cavity of a human subject, and a control section for controlling the insertion section from outside of the body cavity.

In general, the insertion section of an endoscope has an illumination optical system for allowing light from a light source to be emitted toward the inner wall of a body cavity of a human subject, and a distal end portion having an objective optical system for receiving the light which has been reflected from the inner wall. An optical system located at the distal end portion of the endoscope generally comprises a plurality of lenses with spaces defined between adjacent pairs. After the insertion section of the conventional endoscope has been inserted into the body cavity of the human subject, there is the possibility that water vapor present in the gap between adjacent lenses may condense on the surface of each lens, leading to an accumulation of moisture thereon. In practice, the greater the amount of water vapor in the gap, the more liable is the lens to cloud over. When the lens of the optical system becomes clouded over, it is then difficult, if not impossible, to clearly observe a region of interest of the humane subject.

One conceivable method for preventing condensation of water vapor on the lens surface, is for a drying step to be performed in the gap between the lenses. Another method would be for the lens temperature to be kept higher than the ambient temperature. In practice, however, either of these methods is combersome and complicated to carry out.

SUMMARY OF THE INVENTION

It is accordingly the object of this invention to provide an endoscope in which, in order to solve the aforementioned problem, the space between optical members is greatly reduced over the conventional device, in order to prevent water vapor condensation on the surface of the optical members, i.e., the lenses.

An endoscope according to this invention comprises:

an insertion section adapted to be inserted within a body cavity of a human subject, and a control section for controlling the operation of the insertion section;

a distal end portion for insertion in the body cavity of the human subject, the distal end portion having an illumination window for allowing light from an optical source to be emitted toward the inner wall of the body cavity, and an observation window for receiving the light which has been reflected from the inner wall of the body cavity;

light guide means, extending from the insertion section to the control section, for guiding the light from the light source to the illumination window;

an eyepiece section incorporated in the control section, to enable the inner wall of the body cavity to be observed from outside of the body cavity; and image guide means located within the insertion section, for optically connecting the observation window to the eyepiece, in which the light guide means or the image guide means has a light guide path, at least two transparent optical members located along the light guide path, with a space between the optical members, the space being filled with a transparent filling substance.

According to this invention, since a transparent filling substance fills the gap between adjacent optical members situated along the light guide path of the image transmitting means or the light transmitting means, water moisture cannot then condense on the surface of the optical members, due to the elimination of any moisture collection zone.

DESCRIPTION OF THE PREFERRED EMBODIMENTS

Figure 1:
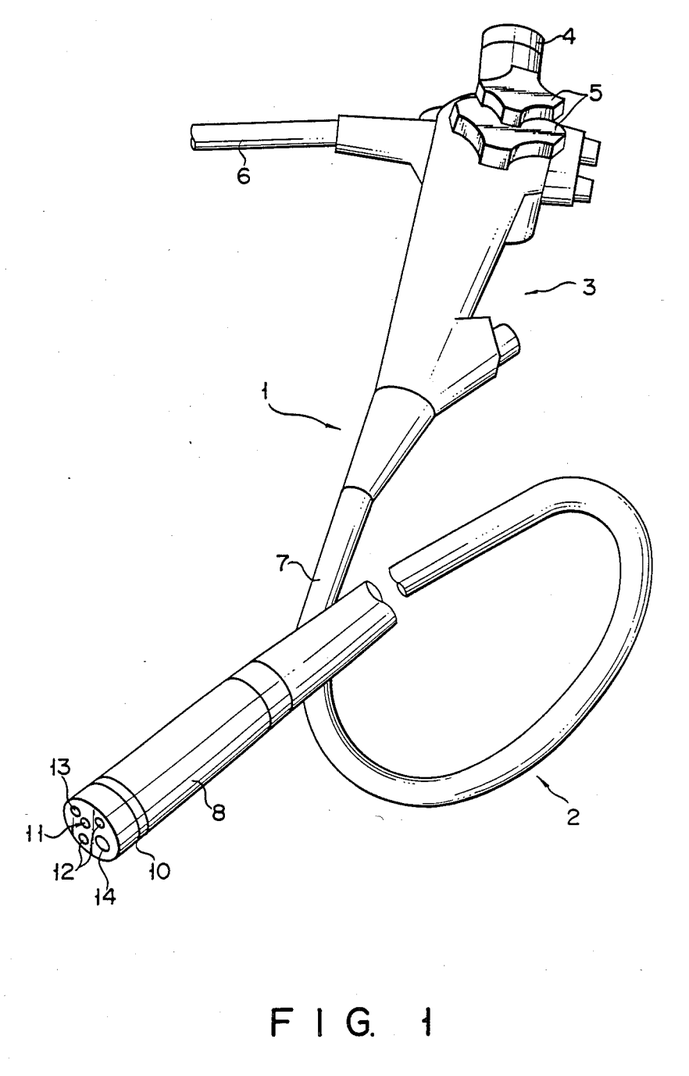
FIG. 1 is a diagrammatic general view of an endoscope according to a first embodiment of this invention.

As shown in FIG. 1, endoscope 1 according to a first embodiment includes insertion section 2 to be inserted into a body cavity and control section 3 coupled to the insertion section. Control section 3 includes eyepiece section 4 and operation knob 5. Universal cord 6 extends from control section 3 and contains a light guide fiber bundle which is optically connectable to an optical source, not shown. Insertion section 2 includes flexible tube section 7 extending from control section 3 and bendable section 8 extending from flexible tube section 8 and operated by operation knob 5 so that it can be bent during the use of the endoscope. Distal end section 10 is provided on the "body cavity" side of bendable section 8 to observe the body cavity. Observation window 11, illumination window 12, nozzle 13 and forceps access hole 14 are provided at the axial end portion of the distal end portion of the endoscope.

Figure 2:
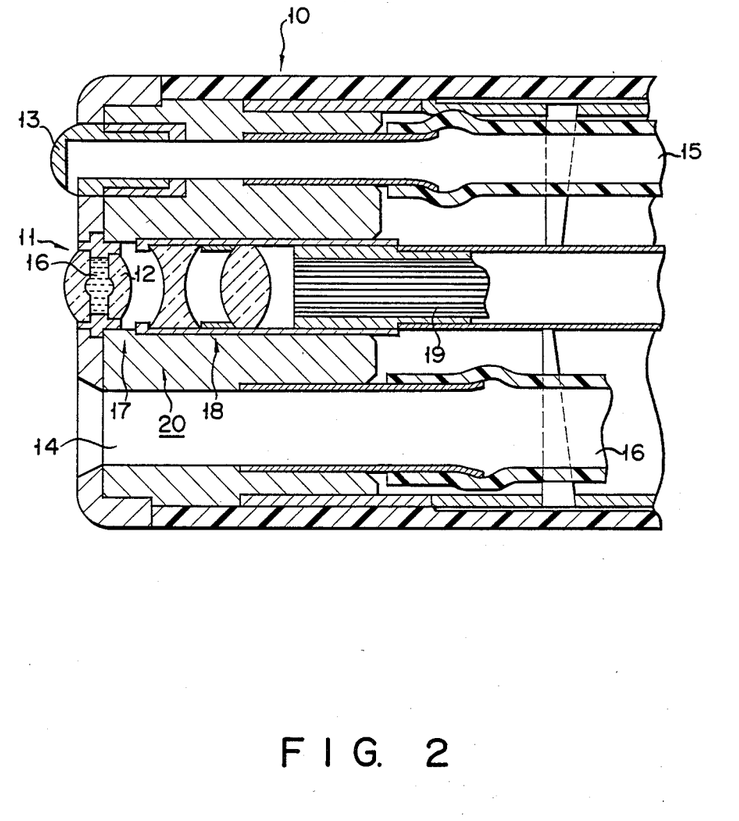
FIG. 2 is a cross-sectional view showing a distal end portion of the endoscope of FIG. 1.

As shown in FIG. 2, nozzle 13 of distal end portion 10 is connected to air/water supply channel 15 and oriented to allow washing water and air which are supplied through air/water supply channel 15 to be jetted onto observation window 11. Forceps access hole 14 is connected to insertion channel 16 for a treatment instrument so that the instrument can be inserted into the body cavity.

Objective optical lens system 20 is fitted in observation window 11 of the insertion section and optically coupled to image guide fiber bundle 19, noting that the aforementioned lens system is comprised of front lens set 17 and rear lens set 18. Image guide fiber bundle 19 is optically connected to the eyepiece lens of eyepiece section 4 as shown in FIG. 1. Between the illumination window and the eyepiece is located objective optical system 20, i.e., front and rear lens sets 17 and 18, and image guide fiber bundle 19, all of which provides an image transmitting means. Illumination window 12, though not shown in FIG. 2, is optically connectable to an optical source through light guide fiber bundle which extends within insertion section 2, control section 3 and universal cord 6 as will be appreciated from FIG. 1. It is, therefore, possible to jet a light beam from the light source onto the inner wall of the body cavity. The light guide fiber bundle provides an optical transmitting means between the optical source and the illumination window.

Figure 3:
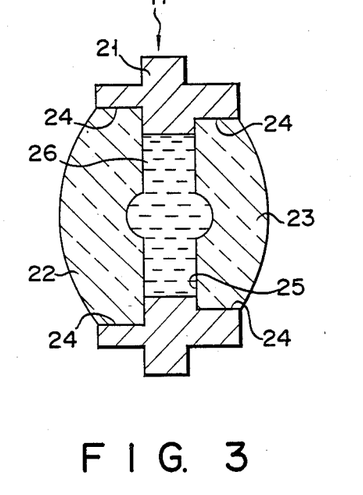
FIG. 3 is a cross-sectional view, partly enlarged, showing a front end lens set in an optical system of the distal end portion of the endoscope of FIG. 2.

As shown in more detail in FIG. 3, front lens set 17 includes first and second lens 22 and 23 located in the cylindrical inner wall of lens frame 21 with a cement layer 24 deposited between the cylindrical interior of lens frame 21 and the first and second lenses. First and second lenses 22 and 23 are of a convex type with hermetically sealed space 25 defined therebetween. Transparent filling substance 26 is contained within space 25 with air completely exhausted. As filling substance 26 use may be made of a gel-like substance commercially available under the trade name of, for example, "Room-Temperature Vulcanizing Silicone Gel KE1052" as manufactured by Shin-Etsu Kagaku Kogyo Co., Ltd. "Room-Temperature Vulcanizing Silicone Gel KE1052" is of a two-liquid type which, when the two liquids are mixed together, becomes cured at about 25° C. in the transparent, colorless gel-like fashion and thus has a transmittance of 95%, refractive index of 1.4, penetration degree of 60 to 70 and adhesion of over 20 g/25 mmW, noting that it contains no water moisture as observable in the ordinary gel. The gel-like substance possesses high viscosity and high heat resistance. As filling substance 26, use may be mad of not only the aforementioned gel-like substance but also, adhesive material, glass, plastics, crystal substance, etc., so long as it can provide a light guide path.

The filling of filling substance 26 into space 25 between first and second lenses 22 and 23 will now be explained below.

From one end of lens frame 21 the first lens is inserted into, and hermetically cemented to the inner wall of, lens frame 21 and, from the other end of lens frame 21, filling substance is filled into the inside of lens frame 21 and then second lens 23 is inserted to hermetically seal the other end of lens frame 21. Although in the aforementioned embodiment the filling substance has been explained as being filled between the two convex lenses, it may be inserted between any proper optical members, if required, such as lenses and prisms.

In the use of endoscope 1, insertion section 2 is inserted into the body cavity of a patient with universal code 6 coupled to the optical source. The light beam from the optical source is transmitted to illumination window 12 of the distal end portion of the endoscope via the light guide fiber bundle which extends within the light guide path of the illumination light transmission system, that is, within a space of universal cord 6, control section 3 and insertion section 2. The light beam is directed through the illumination window to the inner wall of the body cavity. The light beam which is reflected from the inner wall of the body cavity enters observation window 11 and is conducted to the eyepiece of eyepiece section 4 via the light guide path of the image transmission system, i.e., via objective optical system 20 and image guide fiber bundle 19. By so doing, the body cavity is observed and a treatment instrument can be inserted, if required, through forceps access hole 14 so that a region of interest of the patient can be treated.

Since, at front lens set 17 of objective optical system 20, transparent filling substance 26 is filled into space 25 between first and second lenses 22 and 23, there never exists, unlike the prior art, any water moisture in the aforementioned space. As a result, no water moisture is condensed or deposited on the mutually opposite first and second lenses 22 and 23. Filling substance 26 does not degrade the transmittance of objective optical system 20 due to the transparency of that filling substance. Furthermore, where use is made of a gel-like substance of high viscosity as appreciated from the aforementioned embodiment, the ingress of any external water moisture into that location is prevented, owing to the gel-like substance intimately placed in contact with the lens surface and lens frame, so that it is possible to positively prevent the "clouding"phenomenon as encountered with the passage of time.

Figure 4:
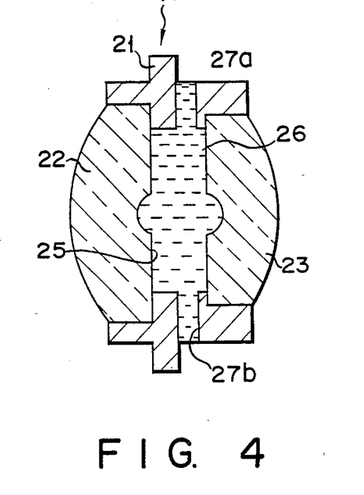
FIG. 4 is a cross-sectional view showing a variant of the front lens set in the optical system of FIG. 3.

FIG. 4 shows a variant of the aforementioned front lens set 17. In this variant, filling hole 27a and discharge hole 27b are formed in the surrounding wall of lens frame 21 with filling hole 27a communicating with space 25. In lens set 17, first and second lenses 22 and 23 are hermetically cemented to the corresponding end portions of the inner hole of lens frame 21 and then filling substance 26 is filled into space 5 through filling hole 27a in which case any excess filling substance can be discharged through discharge hole 27b.

Figure 5:
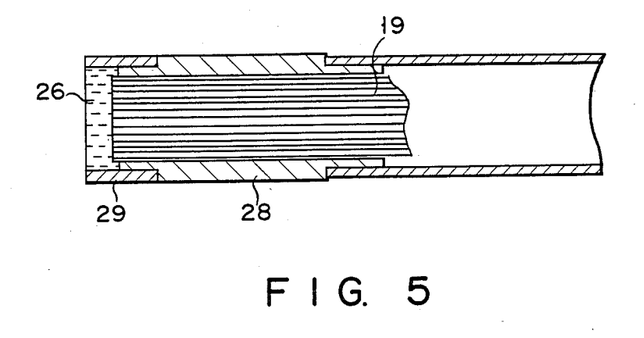
FIG. 5 is a cross-sectional, enlarged view showing an image guide section in an image transmitting system of the distal end portion of the endoscope.

FIG. 5 shows a front end portion of image guide bundle 19 which is optically coupled to objective optical system. Connector 28 is fitted into the distal end portion of image guide fiber bundle 19 such that it is located in the neighborhood of image guide fiber bundle 19. Cylindrical ring 29 is fitted over the distal end portion of connector 28 and extends from the distal end of image guide fiber bundle 19. Transparent filling material 26 which is the same as set out above is filled into a front inner space of cylindrical ring 29 beyond which the distal end of image guide fiber bundle 19 somewhat extends with the exposed end of the filling material flush with the end of cylindrical ring 29.

The specific arrangement as set forth above can prevent water moisture or foreign substance, such as dirt, from being deposited on the forward end of image guide fiber bundle 19. Even if such dirt is deposited on the front end of filling material 26, it never appears within the observer's vision of field due to the front end of the filler material located away from the focal position of objective optical system 20.

FIGS. 6 to 9 show endoscope 30 according to a second embodiment of this invention. The endoscope in this embodiment is of such a type as to be inserted into the blood vessel of a human subject to be examined. In this embodiment, the same transparent material as set forth in connection with the first embodiment is used in a light guide path of a light transmitting means.

Figure 6:
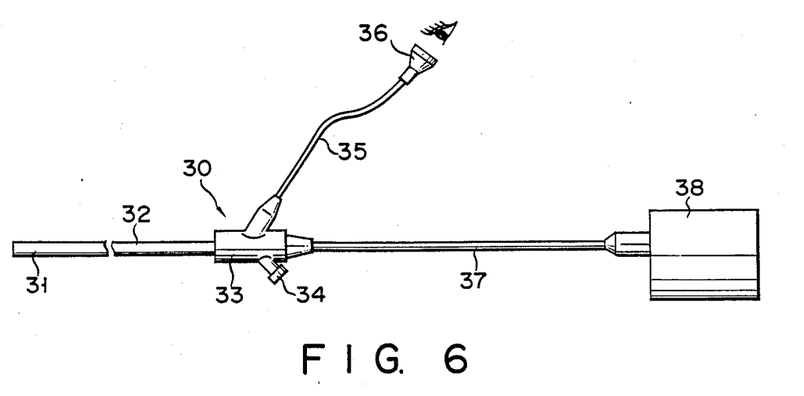
FIG. 6 is a cross-sectional general view of an endoscope according to a second embodiment of this invention.

As shown in FIG. 6, endoscope 30 includes distal end portion 31, insertion section 32 and control (branch)

section 33, as viewed from the left side of that Figure, with passage opening 34 provided at the branch section. Image guide cable 35 and light guide cable 37 extend from branch section 33 with image guide cable 35 conducted to eyepiece section 36 and light guide cable 37 connected to optical source 38.

Figure 7:
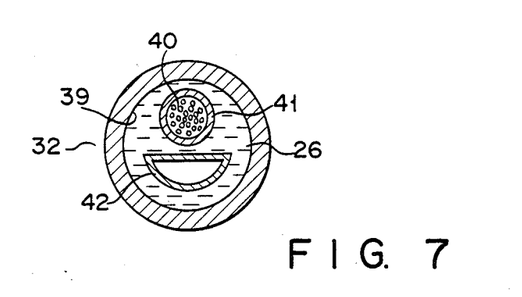
FIG. 7 is a cross-sectional view showing an insertion section of the endoscope of FIG. 6.
Figure 8:
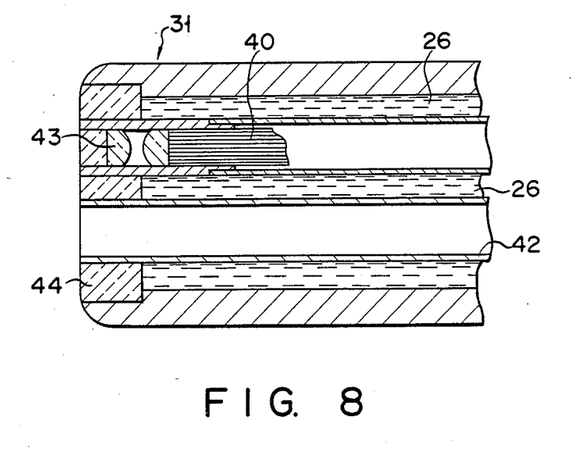
FIG. 8 is a cross-sectional view showing a distal end portion of the endoscope of FIG. 6.
Figure 9:
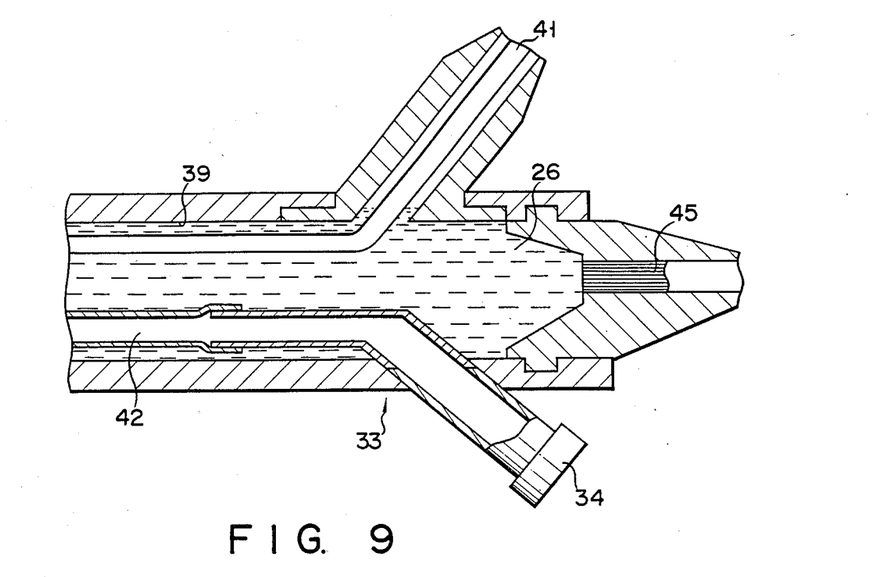
FIG. 9 is a cross-sectional view showing a branch section in an optical system of the endoscope of FIG. 6.

As shown in FIGS. 7 to 9, image guide fiber bundle 40 extends through insertion section 32, distal end portion 31 and branch section 33 in a manner to be covered with tube-like sheath 41. The image guide fiber bundle is optically connected to image guide cable 40 and channel pipe 42 is opened at the distal end portion of the endoscope and communicates with the passage opening of branch section 33. Filling material 26 which is the same as set forth in connection with the transparent filling material is filled within space 39 of distal end portion 31, insertion section 32 and branch section 33 except for the fiber bundle and said pipe.

As shown in FIG. 8, the front end of distal end portion 31 is closely blocked by transparent cover 44 which is made of glass or ceramics, such as transparent alumina ($Al_2O_3$). Objective lens set 43 and channel pipe 42 hermetically extend through transparent cover 44 with objective lens set 43 optically connected to image guide fiber bundle 40.

As shown in FIG. 9, at the rear end (right end portion) of branch section 33, filling material 26 within space 39 is optically connected to light guide fiber bundle 45. The filling material within space 39 and light guide fiber bundle 45 provide a light transmitting means between cover 44 of distal end portion 31 and light source 38.

In use, illumination light which is conducted from light source 38 through light guide cable 45 enters the transparent filling material 26 in space 39 of branch section 33, insertion section 32 and distal end portion 31 of the endoscope and is externally emitted through transparent cover 44 of distal end portion 31. The aforementioned filling material is used in place of a light guide fiber and serves as a light guide path. Filling material 26 is in close contact with the inner surface of space 39 due to its high viscosity as set out above and can prevent the water moisture from entering into endoscope 30. Since no use is made of any light guide fiber, insertion section 32 of the endoscope can be so formed as to have a very small cross-section. Further, insertion section 32 can be flexibly formed due to the gel-like nature of the filling material.

Figure 10:
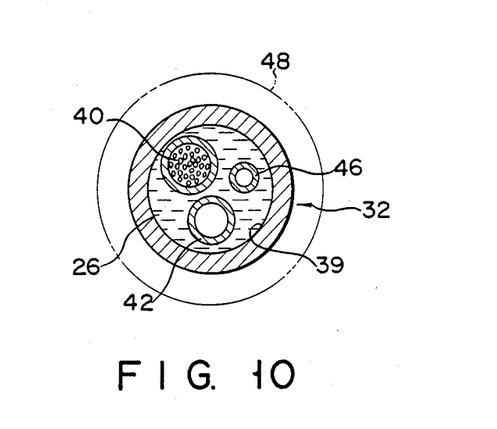
FIG. 10 is a view similar to that of the variant of the endoscope of the second embodiment.

FIG. 10 is a partial cross-sectional view showing a variant of the aforementioned second embodiment. In this variant, balloon 48 is detachably mounted on the outer periphery of the distal end portion of the endoscope. Fluid supply/discharge tube 46 is provided over the range of insertion section 32 and branch section 33 to allow the fluid to be supplied to, and discharged from, the balloon. In addition to this, a channel may be provided for the other purpose. In this variant, filling material 26 is filled into space 39 except for fiber bundle 40 and pipe 42.

Figure 11:
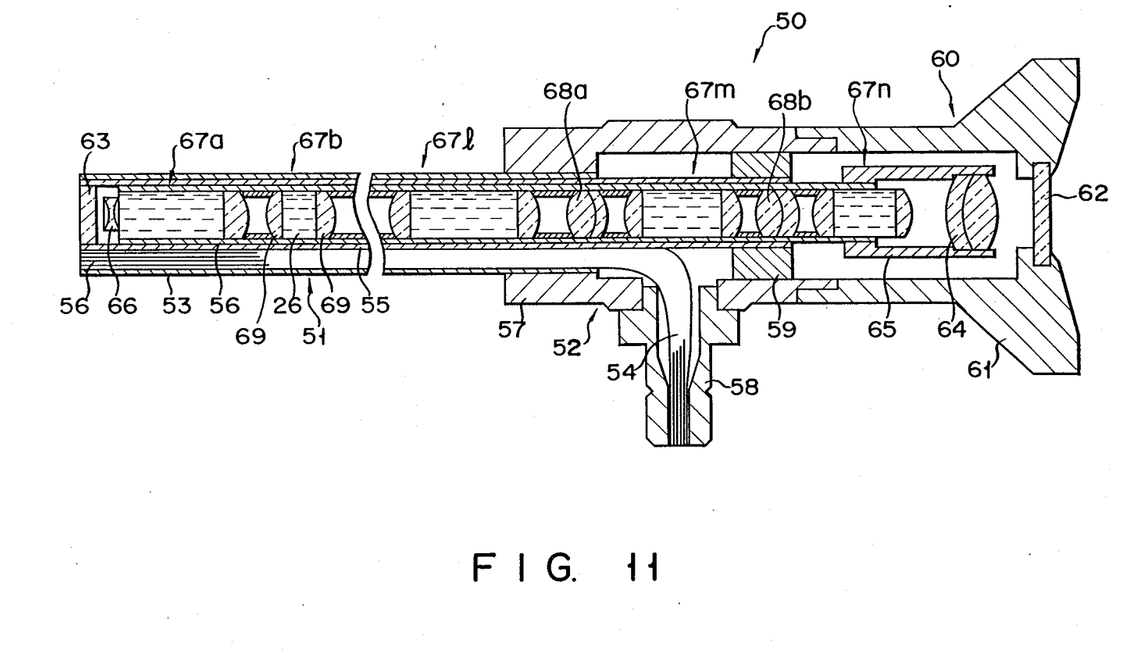
FIG. 11 is a cross-sectional view showing a third embodiment of this invention.

FIG. 11 shows endoscope 50 according to a third embodiment of this invention. In this embodiment, the transparent filling material which is the same as set out in connection with the aforementioned embodiment is used as a light guide path for an image transmitting system.

Endoscope 50 is of a rigid type having elongated section 51, which is inserted into the body cavity of a human subject, and control section 52. Insertion section 51 has thin-walled outer tube 53 made of a rigid material, such as a metal, which has light guide fiber bundle 54 and thin-walled inner tube 55 made of a rigid material as that of outer tube 53.

Control section 52 includes control section body 57 for supporting the insertion section and control section body 57 has connector 58 for connecting light guide fiber 54 within the insertion section to an optical source, not shown, and fixed block 59 for fixing inner tube 55 in place. Eyepiece section 60 is fitted in place at the rear end of control section 52, that is, at that far end located opposite to insertion section 51.

Eyepiece section 60 has eyepiece 61 attached to control operation body 57 and eyepiece cover glass 62 mounted on the rear end portion of the eyepiece.

As shown in FIG. 11, within inner tube 55 extending within outer tube 53 of the insertion section is provided lens tube 56 which extends up to eyepiece 61 of the eyepiece section past control section body 57. The distal end of lens tube 56 which is located on the side opposite to that in which the eyepiece section is provided, is covered with cover glass 63. That proximal end portion of lens tube 56 located on the eyepiece section side is closed by eyepiece lens frame 65 having eyepiece lens 64 fitted therein. An optical system comprised of a plurality of lenses is provided between the distal end and the proximal end of the lens tube 56.

The image transmitting means of this embodiment is comprised of an optical lens array between objective 66 and eyepiece 64 which is comprised of elongated rod lens 67a, 67b, 67l, 67m and 67n and combination lenses 68a and 68b. Of rod lenses 67a, 67b, 67l, 67m and 67n, the rod lens as typically identified by reference numeral 67b is comprised of convex lenses 69, 69 made of glass and transparent substance 26 filled between convex lenses 69 and 69 in which case the transparent substance is the same as set forth in connection with the aforementioned embodiment.

The filling substance, that is, the gel-like substance is in close contact with the inner surface of lens tube 56 due to its high viscosity, thus preventing any water moisture from entering into a space between glass lenses 68. In particular, the space between rod lenses 67a and 67n can be filled with filling material 26 to provide a hermetic seal within lens tube 56. Further, the filling material is lighter in weight than glass, resulting in an inexpensive low-weight unit because of the presence of that low-weight rod lenses. Where the rod lens comprised of an elongated glass is incorporated into the endoscope, there is a risk that it can be broken when control section 51 is bent, even though slightly. According to this invention such a risk can be avoided because gel-like substance 26 is used as the rod lens of this application.

Figure 12:
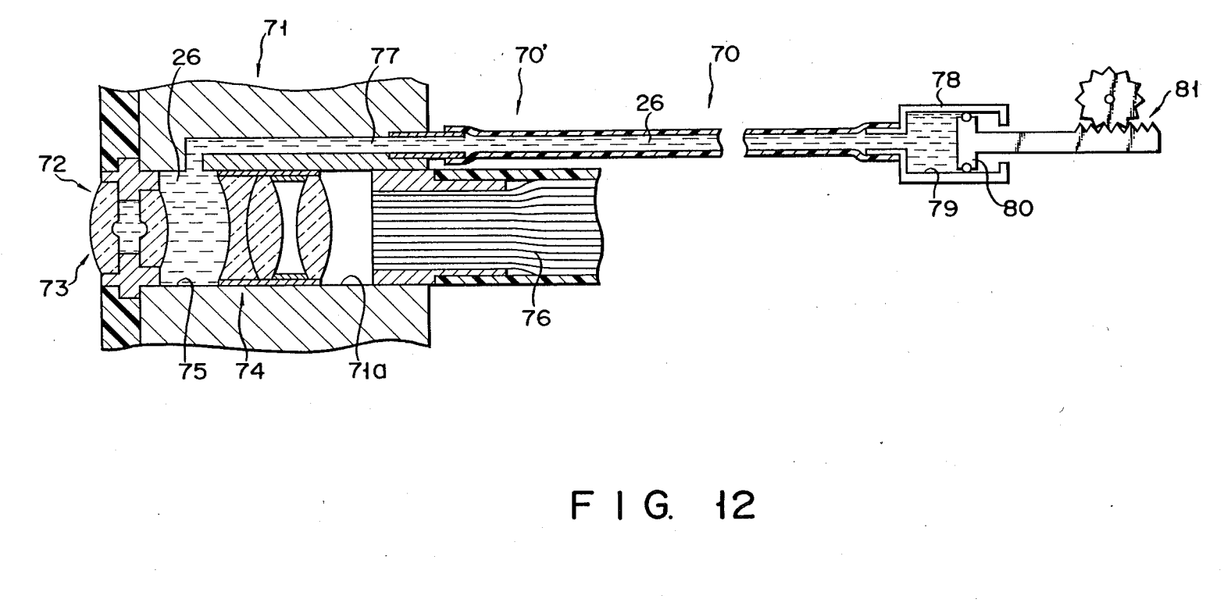
FIG. 12 is a cross-sectional view showing a fourth embodiment of this invention.

FIG. 12 shows endoscope 70 according to a fourth embodiment of this invention. In this embodiment, since a filling substance which is the same as set forth in connection with the aforementioned embodiment is employed to provide a light guide path for an objective optical system as an image transmitting means, it is possible to provide a focusing or zooming mechanism.

Objective optical system 72 at distal end portion 71 of insertion section 70' is comprised of front lens set 73 and rear lens set 74 both located within inner hole 71 of the distal end portion of the endoscope, and is optically connected to image guide fiber 76. As in the case of front lens set 17 in the first embodiment of this invention, front lens set 73 is comprised of a pair of lenses fitted within the lens frame and a filling substance filled between the pair of lenses. The rear lens set is comprised of a pair of convex lenses and single concave lens and can be moved in an axial direction within inner hole 71a of the distal end portion. Between front lens set 73 and rear end lens set 74 is formed storage chamber 75 for storing a filling substance of a variable capacity. The filling substance is the same as set forth in connection with the aforementioned embodiment of this invention and filled within the chamber, so that it is supplied into, and discharged out of, cylinder 78.

Cylinder 78 has chamber 79 for storing the filling substance and piston 80 provided within cylinder chamber 79 such that it can be slidably moved there. Piston 80 is movable within cylinder chamber 79 by actuating mechanism 81 which is comprised of a rack and pinion.

When piston 80 is pushed by actuating mechanism 81 into cylinder chamber 79, the filling substance is supplied from within cylinder 79 through channel 77 into storage chamber 75, so that rear lens set 74 is moved toward image guide fiber 76. When piston 80 is pulled relative to cylinder chamber 79, a negative pressure is formed within the cylinder chamber, causing the filling substance within storage chamber 75 to be sucked into cylinder chamber 79 with the result that rear lens set 74 is advanced toward front lens set 73.

As a result, that air-layer zone which might otherwise cause clouding to occur on the surface of lenses and objective optical system 72 is decreased according to this invention. Further, the focal distance, or the amplification, of objective optical system 72 can also be varied due to a variation in the amount of filling substance within storage chamber 75.

Although the aforementioned respective embodiment has been explained in conjunction with the image guide fiber bundle and optical lens system as an image transmitting means, a solid state image sensing device, such as a CCD, may be employed for the same purpose. Further, the filling substance, that is, the gel-like substance may be filled at a location not only between the lenses but also between the lens and the prism, thereby preventing a collection of water moisture on the optical members which might otherwise occur at that place. The filling substance may be stained and thus serve as anti-clouding substance for the optical members and as a color filter.

Although this invention has been explained in conjunction with some embodiments, it can be changed or modified in a variety of ways within the spirit and scope thereof.

What is claimed is:

1. An endoscope comprising:
    an insertion section adapted to be inserted within a body cavity of a human subject, and a control section for controlling the operation of the insertion section;
    a distal end portion for insertion in the body cavity of the human subject,
    said distal end portion having an illumination window for allowing light from an optical source to be emitted toward the inner wall of the body cavity, and an observation window for receiving the light which has been reflected from the inner wall of the body cavity;
    light guide means, extending from the insertion section to the control section, for guiding the light from the light source to the illumination window;
    an eyepiece section located at the control section, to enable the inner wall of the body cavity to be observed from outside of the body cavity;
    image guide means located within the insertion section, for optically connecting the observation window to the eyepiece; and
    at least two transparent optical members located between the observation window and the image guide means, said optical members being spaced from one another, said space being filled with a transparent, highly viscous gel-like substance.

2. The endoscope according to claim 1, wherein said optical members are each comprised of a lens and said gel-like substance contains no water moisture.

3. The endoscope according to claim 2, wherein said image guide means includes an objective optical system, arranged at said distal end portion, and an image guide fiber bundle for optically connecting said objective optical system to said eyepiece section; said objective optical system includes a front lens set and a rear lens set; and said front lens set includes a cylindrical lens frame and a pair of lenses fitted in the lens frame, to constitute an optical member for said image guide means.

4. The endoscope according to claim 3, wherein said cylindrical lens frame has at least one opening through which said filling substance is supplied into, or discharged from, the cylindrical lens frame.

* * * * *